United States Patent [19]
Andree et al.

[11] Patent Number: 5,658,857
[45] Date of Patent: Aug. 19, 1997

[54] IMIDAZOAZINES

[75] Inventors: Roland Andree, Langenfeld, Germany; Hans-Joachim Santel, Cansas City, Kans.; Markus Dollinger, Leverkusen, Germany

[73] Assignee: Bayer Aktiengesellschaft, Leverkusen, Germany

[21] Appl. No.: 500,993
[22] PCT Filed: Feb. 2, 1994
[86] PCT No.: PCT/EP94/00296
  § 371 Date: Aug. 8, 1995
  § 102(e) Date: Aug. 8, 1995
[87] PCT Pub. No.: WO94/18198
  PCT Pub. Date: Aug. 18, 1994

[30] Foreign Application Priority Data

Feb. 15, 1993 [DE] Germany ............ 43 04 454.9
Aug. 12, 1993 [DE] Germany ............ 43 27 027.1

[51] Int. Cl.$^6$ ............ A01N 43/90; C07D 471/04
[52] U.S. Cl. ............ 504/228; 504/236; 504/246; 544/184; 544/236; 544/281; 544/350; 546/121
[58] Field of Search ............ 546/121; 544/184, 544/236, 281, 350; 504/228, 236, 246

[56] References Cited

FOREIGN PATENT DOCUMENTS 4120108 12/1992 Germany.
93/15074 8/1993 WIPO.

Primary Examiner—Bernard Dentz
Attorney, Agent, or Firm—Sprung Horn Kramer & Woods

[57] ABSTRACT

The invention relates to new imidazoazines of the general formula (I)

in which $R^1, R^2, R^3, R^4, R^5, R^6$, A, D, E and G have the meanings given in the description, to processes for their preparation, and to their use as herbicides.

11 Claims, No Drawings

IMIDAZOAZINES

This application is a 371 of PCT/EP94/00296 filed Feb. 2, 1994, published as WO94/8198 Aug. 18, 1994.

The invention relates to new imidazoazines, to processes for their preparation and to their use as herbicides.

It has already been disclosed that certain 2-aryl-5,6,7,8-tetrahydro-imidazo-[1.2-a]pyridines have herbicidal properties (cf. DE-OS [German Published Specification] 4120108).

Some imidazoazines are described in the literature without any information having been disclosed on their herbicidal properties (cf. J. Med. Chem. 8 (1965), 305–312—cited in Chem. Abstracts 62:16228a; Khim. Geterotsikl. Soedin 1978, 258–262—cited in Chem. Abstracts 88: 190733d; J. Heterocycl. Chem. 25 (1988), 129–137–cited in Chem. Abstracts 110: 237891; Khim. Geterotsikl. Soedin 1991, 810–816—cited in Chem. Abstracts 116: 128842g).

There have now been found new imidazoazines of the general formula (I)

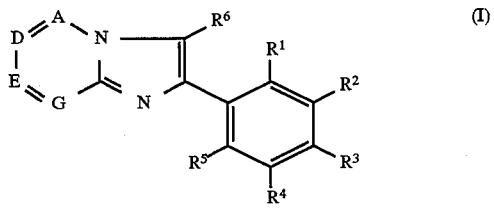

in which
- $R^1$ represents hydrogen, halogen, cyano, carboxyl, carbamoyl, nitro, alkyl, halogenoalkyl, alkoxy or halogenoalkoxy,
- $R^2$ represents hydrogen, halogen, cyano, carboxyl, nitro, hydroxyl, mercapto, amino, carbamoyl, sulpho, sulphamoyl, chlorosulphonyl, or represents in each case optionally substituted alkyl, alkenyl, alkinyl, alkoxy, alkenyloxy, alkinyloxy, alkylthio, alkenylthio, alkinylthio, alkylsulphinyl, alkylsulphonyl, alkylaminosulphonyl, dialkylaminosulphonyl, alkylamino, dialkylamino, alkenylamino, alkinylamino, alkylsulphonylamino, N-alkyl-alkylsulphonylamino, alkoxycarbonyl, alkoxyaminosulphonyl, N-alkyl-alkoxy-aminosulphonyl, arylsulphonylamino, arylalkylsulphonylamino, N-alkyl-arylsulphonylamino, N-alkylarylalkylsulphonylamino, arylaminosulphonyl, arylalkylaminosulphonyl, N-alkylarylaminosulphonyl or N-alkylarylalkylaminosulphonyl,
- $R^3$ represents hydrogen, halogen, cyano, carboxyl, amino, hydroxyl, carbamoyl, nitro, or represents in each case optionally substituted alkyl, alkenyl, alkinyl, alkoxy, alkenyloxy, alkinyloxy, alkylthio, alkinylthio, alkylsulphinyl, alkylsulphonyl, alkylamino, alkenylamino, alkinylamino, alkylsulphonylamino or alkoxycarbonyl,
- $R^4$ represents hydrogen, halogen, cyano, alkyl or halogenoalkyl,
- $R^5$ represents hydrogen, halogen, cyano, alkyl or halogenoalkyl,
- $R^6$ represents halogen, cyano, nitro, amino, alkoxy, alkylthio, alkylsulphinyl, alkylsulphonyl, alkylamino or dialkylamino,
- A represents nitrogen or the group C—$R^7$,
- D represents nitrogen or the group C—$R^8$,
- E represents nitrogen or the group C—$R^9$ and
- G represents nitrogen or the group C—$R^{10}$, where $R^7$, $R^8$, $R^9$ and $R^{10}$ are identical or different and in each case represent hydrogen, halogen, cyano, carboxyl, carbamoyl, nitro, or in each case optionally substituted alkyl, phenyl, alkoxy, alkylthio, alkylsulphinyl, alkylsulphonyl, alkylamino, dialkylamino or alkoxycarbonyl, and acid addition products of the compounds of the formula (I), with the proviso that at least one of the radicals $R^1$ to $R^5$ is other than hydrogen and that the following compounds are excepted by disclaimer:

3-bromo-2-(4-methylsulphonyl-phenyl)-imidazo-[1,2-a]-pyridine (known from Chem. Abstracts 62:16228a), 3-bromo-2-(4-formyl-phenyl)-imidazo-[1,2-a]-pyridine (known from Chem. Abstracts 110: 23789t), 3-bromo-2-(4-nitro-phenyl)-imidazo-[1,2-a]pyridine (known from Chem. Abstracts 88: 190733d), 3-chloro-2-(4-bromo-phenyl)-imidazo-[1,2-a]-pyridine, 3-chloro-2-(4-chloro-phenyl)-imidazo-[1,2-a]-pyridine, 3-chloro-2-(4-methoxy-phenyl)-imidazo-[1,2-a]-pyridine, 3-bromo-2-(4-bromo-phenyl)-imidazo-[1,2-a]-pyridine and 3-bromo-2-(4-methoxy-phenyl)-imidazo-[1,2-a]-pyridine (all known from Chem. Abstracts 116: 128842g).

The new imidazoazines of the general formula (I) are obtained when, (a) in the event that, in formula (I), $R^6$ represents halogen or nitro and $R^1$, $R^2$, $R^3$, $R^4$ and $R^5$ as well as A, D, E and G have the abovementioned meanings, imidazoazines of the general formula (II)

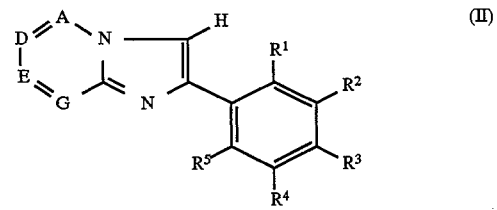

in which
$R^1$, $R^2$, $R^3$, $R^4$, $R^5$, A, D, E and G have the abovementioned meanings, are reacted with halogenating agents or nitrating agents, if appropriate in the presence of inert diluents, or when, (b) in the event that, in formula (I), $R^6$ represents amino, cyano, alkoxy, alkylthio, alkylsulphinyl, alkylsulphonyl, alkylamino or dialkylamino and $R^1$, $R^2$, $R^3$, $R^4$, $R^5$, A, D, E and G have the abovementioned meanings, halogenated imidazoazines of the general formula (Ia)

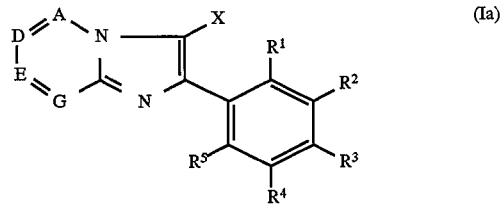

in which
X represents halogen and
$R^1$, $R^2$, $R^3$, $R^4$, $R^5$, A, D, E and G have the abovementioned meanings, are reacted with ammonia or with alkali metal cyanides or with alcohols, alkylmercaptans, alkylamines or dialkylamines or with their alkali metal salts, if appropriate in the presence of diluents, and, if appropriate—to prepare corresponding alkylsulphinyl or alkysulphonyl compounds—, the product is subsequently oxidized by customary methods, and when, if appropriate—to prepare acid addition products of the compounds of the formula (I)—, the compounds obtained in accordance with process (a) or (b) are reacted with acids by customary methods.

Other customary methods may also be used for converting the compounds of the formula (I) into different compounds of the formula (I) in accordance with the above definition, for example by electrophilic substitution (for example $R^3$: H→$NO_2$, $SO_3H$, $SO_2Cl$), nucleophilic substitution (for example $R_3$: F→$OCH_3$) or other conversions of functional groups (for example $R^3$: $NO_2$=$NH_2$ and, if appropriate, subsequently →$NHSO_2R$)—cf. also the preparation examples.

The new imidazoazines of the general formula (I) are distinguished by a powerful herbicidal activity. Even the compounds of the formula (I) which are excepted above by disclaimer display a good herbicidal activity.

In the definitions, the saturated or unsaturated hydrocarbon chains, such as, for example, alkyl or alkenyl, also in connection with hetero atoms, such as, for example, in alkoxy or alkenyloxy, are in each case straight-chain or branched. Halogen generally represents fluorine, chlorine, bromine or iodine, preferably fluorine, chlorine or bromine, in particular fluorine or chlorine.

The invention preferably relates to compounds of the formula (I) in which $R^1$ represents hydrogen, fluorine, chlorine, bromine, cyano, carboxyl, carbamoyl, nitro, or represents alkyl or alkoxy, each of which has 1 to 4 carbon atoms and each of which is optionally substituted by fluorine or chlorine, $R^2$ represents hydrogen, fluorine, chlorine, bromine, cyano, carboxyl, carbamoyl, nitro, hydroxyl, mercapto, amino, sulpho, sulphamoyl, chlorosulphonyl, or represents alkyl, alkoxy, alkylthio or alkylamino, each of which has 1 to 6 carbon atoms and each of which is optionally substituted by fluorine, chlorine, cyano, carboxyl, carbamoyl or $C_1$-$C_4$-alkoxy-carbonyl, $R^2$ furthermore represents alkenyl, alkinyl, alkenyloxy, alkinyloxy, alkenylthio, alkinylthio, alkenylamino or alkinylamino, each of which has 3 to 6 carbon atoms and each of which is optionally substituted by fluorine, chlorine, bromine, cyano, carboxyl, carbamoyl or $C_1$-$C_4$-alkoxy-carbonyl, $R^2$ furthermore represents alkylsulphinyl, alkylsulphonyl, alkylsulphonylamino, N-alkyl-alkylsulphonylamino, alkylaminosulphonyl, dialkylaminosulphonyl, alkoxyaminosulphonyl, N-alkyl-alkoxyaminosulphonyl, dialkylamino or alkoxycarbonyl, each of which has up to 6 carbon atoms in the alkyl groups and each of which is optionally substituted by fluorine or chlorine, $R^2$ furthermore represents in each case optionally substituted phenylsulphonylamino, phenyl-$C_1$-$C_4$-alkylsulphonylamino, N—$C_1$-$C_4$-alkyl-phenylsulphonylamino, N—$C_1$-$C_4$-alkyl-phenyl-$C_1$-$C_4$-alkyl-sulphonylamino, phenylaminosulphonyl, phenyl-$C_1$-$C_4$-alkyl-aminosulphonyl, N—$C_1$-$C_4$-alkyl-phenylaminosulphonyl or N—$C_1$-$C_4$-alkyl-phenyl-$C_1$-$C_4$-alkyl-aminosulphonyl, it being possible for the phenyl groups in each case optionally to contain the following substituents: fluorine, chlorine, bromine, iodine, cyano, nitro, hydroxyl, amino, carboxyl, carbamoyl, and in each case optionally fluorine- and/or chlorine-substituted $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkoxycarbonyl or phenyl.

$R^3$ represents hydrogen, fluorine, chlorine, bromine, cyano, carboxyl, amino, hydroxyl, carbamoyl, nitro, or represents alkyl, alkoxy, alkylthio or alkylamino, each of which has 1 to 6 carbon atoms and each of which is optionally substituted by fluorine, chlorine, cyano, carboxyl, carbamoyl or $C_1$-$C_4$-alkoxycarbonyl, $R^3$ furthermore represents alkenyl, alkinyl, alkenyloxy, alkinyloxy, alkenylthio, alkinylthio, alkenylamino or alkinylamino, each of which has 3 to 6 carbon atoms and each of which is optionally substituted by fluorine, chlorine, bromine, cyano, carboxyl, carbamoyl or $C_1$-$C_4$-alkoxy-carbonyl, or represents alkylsulphinyl, alkylsulphonyl, alkylsulphonylamino or alkoxycarbonyl, each of which has up to 6 carbon atoms and each of which is optionally substituted by fluorine or chlorine, $R^4$ represents hydrogen, fluorine, chlorine, bromine, cyano, or represents alkyl having 1 to 6 carbon atoms which is optionally substituted by fluorine or chlorine, $R^5$ represents hydrogen, fluorine, chlorine, bromine, cyano, or represents alkyl having 1 to 4 carbon atoms which is optionally substituted by fluorine or chlorine, $R^6$ represents chlorine, bromine, iodine, cyano, nitro, amino, or represents alkoxy, alkylthio, alkylsulphinyl, alkylsulphonyl, alkylamino or dialkylamino, each of which has 1 to 6 carbon atoms in the alkyl groups, A represents nitrogen or the group C—$R^7$, D represents nitrogen or the group C—$R^8$, E represents nitrogen or the group C—$R^9$ and G represents nitrogen or the group C—$R^{10}$, where $R^7$, $R^8$, $R^9$ and $R^{10}$ are identical or different and each of which represents hydrogen, fluorine, chlorine, bromine, cyano, carboxyl, carbamoyl, nitro, or in each case optionally fluorine- or chlorine-substituted alkyl, phenyl, alkoxy, alkylthio, alkylsulphinyl, alkylsulphonyl, alkylamino, dialkylamino or alkoxycarbonyl, the alkyl radicals in each case containing 1 to 6 carbon atoms, with the proviso that at least one of the radicals $R^1$ to $R^5$ is other than hydrogen and with the exception of the compounds excluded above by disclaimer.

The invention furthermore provides acid addition products of compounds of the formula (I), preferably with protonic acids, such as, for example, hydrochloric acid, hydrobromic acid, hydriodic acid, sulphuric acid, methanesulphonic acid, benzenesulphonic acid, toluenesulphonic acid, p-dodecylbenzene acid and naphthalene-1,5-disulphonic acid, in particular with hydrohalic acids, such as, for example, hydrochloric acid and hydrobromic acid.

The invention particularly relates to compounds of the formula (I) in which $R^1$ represents hydrogen, fluorine, chlorine, bromine, cyano, nitro, methyl, ethyl or trifluoromethyl, $R^2$ represents hydrogen, fluorine, chlorine, bromine, cyano, carboxyl, carbamoyl, nitro, hydroxyl, mercapto, amino, sulpho, sulphamoyl, chlorosulphonyl, or represents methyl, ethyl, propyl, methoxy, ethoxy, propoxy, methylthio, ethylthio, propylthio, methylamino, ethylamino or propylamino, each of which is optionally substituted by fluorine, chlorine, cyano, carboxyl, carbamoyl, methoxycarbonyl or ethoxycarbonyl, $R^2$ furthermore represents allyl, propargyl, allyloxy, propargyloxy, allylthio, propargylthio, dimethylamino, allylamino or propargylamino, each of which is optionally substituted by fluorine, chlorine, cyano, carboxyl, methoxycarbonyl or ethoxycarbonyl, or represents methylsulphinyl, ethylsulphinyl, methylsulphonyl, ethylsulphonyl, methylsulphonylamino, ethylsulphonylamino, n- or i-propylsulphonylamino, methylaminosulphonyl, ethylaminosulphonyl, n- or i-propylaminosulphonyl, dimethylaminosulphonyl, diethylaminosulphonyl, dipropylaminosulphonyl, phenylsulphonylamino, tolylsulphonylamino, phenylaminosulphonyl, tolylaminosulphonyl, methoxycarbonyl or ethoxycarbonyl, each of which is optionally substituted by fluorine or chlorine, $R^3$ represents hydrogen, fluorine, chlorine, bromine, cyano, carboxyl, amino, hydroxyl, carbamoyl, nitro, or represents methyl, ethyl, n- or i-propyl, n-, i-, s- or t-butyl, methoxy, ethoxy, propoxy, methylthio, ethylthio, propylthio, methylamino, ethylamino or propylamino, each of which is optionally substituted by fluorine, chlorine, cyano, carboxyl, carbamoyl, methoxycarbonyl or ethoxycarbonyl, $R^3$ furthermore represents allyl, propargyl, allyloxy, propargyloxy, allylthio, propargylthio, allylamino or propargylamino, each of which is optionally substituted by fluorine, chlorine, cyano, carboxyl, methoxycarbonyl or ethoxycarbonyl, or represents methylsulphinyl, ethylsulphinyl, methylsulphonyl, ethylsulphonyl, methylsulphonylamino, ethylsulphonylamino, methoxycarbonyl or ethoxycarbonyl, each of which is optionally substituted by fluorine or chlorine, $R^4$ represents hydrogen, fluorine, chlorine, bromine, cyano, methyl, ethyl or trifluoromethyl, $R^5$ represents hydrogen, fluorine, chlorine, bromine, cyano, methyl, ethyl or trifluoromethyl, $R^6$ represents chlorine, bromine, cyano, nitro, amino, methoxy, ethoxy, methylthio, ethylthio, methylsulphinyl, ethylsulphinyl, methylsulphonyl, ethylsulphonyl, methylamino or dimethylamino, A represents nitrogen or the group $C-R^7$, D represents nitrogen or the group $C-R^8$, E represents nitrogen or the group $C-R^9$ and G represents nitrogen or the group $C-R^{10}$, where $R^7$, $R^8$, $R^9$ and $R^{10}$ are identical or different and in each case represent hydrogen, fluorine, chlorine, bromine, cyano, carboxyl, carbamoyl, nitro, or in each case optionally fluorine- or chlorine-substituted methyl, ethyl, n- or i-propyl, phenyl, methoxy, ethoxy, methylthio, ethylthio, methylsulphinyl, ethylsulphinyl, methylsulphonyl, ethylsulphonyl, methylamino, ethylamino, dimethylamino, diethylamino, methoxycarbonyl or ethoxycarbonyl, with the proviso that at least one of the radicals $R^1$ to $R^5$ is other than hydrogen and with the exception of the compounds excluded above by disclaimer.

A particularly preferred group of compounds according to the invention is formed by those compounds of the formula (I) in which A represents the group $C-R^7$, D represents the group $C-R^8$, E represents the group $C-R^9$ and G represents the group $C-R^{10}$, where $R^1$, $R^2$, $R^3$, $R^4$, $R^5$, $R^6$, $R^7$, $R^8$, $R^9$ and $R^{10}$ have the meanings given above as being particularly preferred, with the proviso that at least one of the radicals $R^1$ to $R^5$ is other than hydrogen and with the exception of the compounds excluded above by disclaimer.

Another particularly preferred group of compounds according to the invention is formed by those compounds of the formula (I) in which A represents nitrogen, D represents the group $C-R^8$, E represents the group $C-R^9$ and G represents the group $C-R^{10}$, where $R^1$, $R^2$, $R^3$, $R^4$, $R^5$, $R^6$, $R^8$, $R^9$ and $R^{10}$ have the meanings given above as being particularly preferred, with the proviso that at least one of the radicals $R^1$ to $R^5$ is other than hydrogen.

The definitions of radicals given above in general terms or where preferred ranges have been indicated apply to the end product of the formula (I) and accordingly to the starting substances required for their preparation. These definitions of radicals can be combined with each other as desired, that is to say combinations between the preferred ranges are also possible.

If, for example, 2-(4-cyano-2-fluoro-5-trifluoromethyl-phenyl)-imidazo-[1,2-a]-pyridine and chlorine are used as starting substances, the course of the reaction in process (a) according to the invention can be outlined by the following equation:

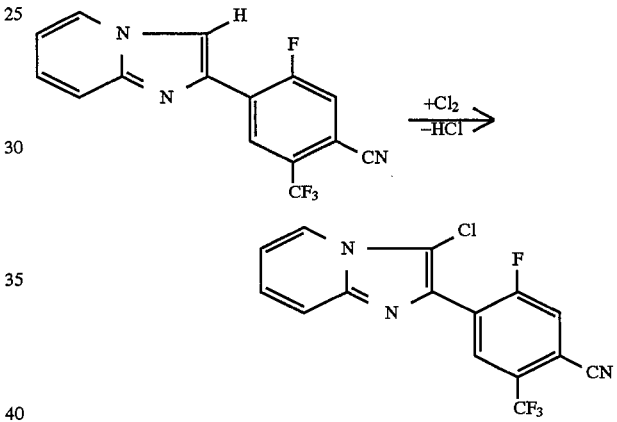

If, for example, 3-bromo-2-(3-ethoxy-4-methyl-phenyl)-imidazo-[1,2-a]-pyridine and sodium methylate are used as starting substances, the course of the reaction in process (b) according to the invention can be outlined by the following equation:

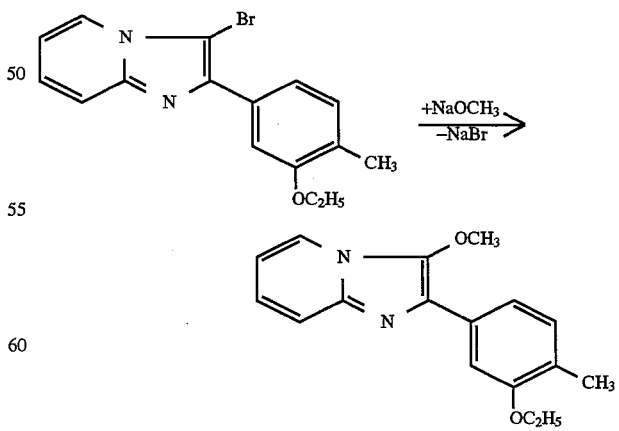

The imidazoazines of the formula (II) to be used as starting substances in process (a) according to the invention are known and/or can be prepared by processes known per se (cf. J. Heterocycl. Chem. 25 (1988), 129–137; Khim. Geterotsikl. Soedin 1979, 258–262—cited in Chem. Abstracts 88: 190733d; J. Med. Chem. 8 (1965), 305–312—cited in Chem. Abstracts 62: 16228a; Liebigs Ann. Chem. 699 (1966), 112–126; preparation examples).

Process (a) according to the invention is carded out using halogenating agents. Suitable halogenating agents are the pure halogens, in particular, chlorine, bromine or iodine, or suitable halogen compounds, such as, for example, N-chloro- or N-bromo-succinimide, hydrogen bromide or hydrogen iodide (the latter substances in the presence of an oxidant, such as dimethyl sulphoxide).

If appropriate, process (a) according to the invention is carried out using nitrating agents. The preferred nitrating agent is concentrated nitric acid, if appropriate in the presence of sulphuric acid.

Processes (a) and (b) according to the invention for the preparation of the new imidazoazines of the formula (I) are preferably carried out using diluents. Suitable diluents are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, Such as diethyl ether and dibutyl ether, glycol dimethyl ether and diglycol dimethyl ether, tetrahydrofuran and dioxane, alcohols, such as methanol and ethanol, ketones, such as acetone, methyl ethyl ketone, methyl isopropyl ketone and methyl isobutyl ketone, carboxylic acids, such as acetic acid and propionic acid, esters, such as methyl acetate and ethyl acetate, nitrides, such as, for example, acetonitrile and propionitrile, amides, such as, for example, dimethylformamide, dimethylacetamide and N-methylpyrrolidone, and also dimethyl sulphoxide, tetramethylene sulphone and hexamethylphosphoric triamide.

When carrying out processes (a) and (b) according to the invention, the reaction temperatures can be varied within a substantial range. In general, the processes are carried out at temperatures between 0° C. and 150° C., preferably at temperatures between 10° C. and 100° C.

Processes (a) and (b) according to the invention are generally carded out under atmospheric pressure. However, it is also possible to carry out the processes under elevated or reduced pressure.

For carrying out processes (a) and (b) according to the invention, the starting substances required in each case are generally employed in approximately equimolar mounts. However, it is also possible to use one of the two components employed in each case in a larger excess. In general, the reactions are carded out in a suitable diluent, and the reaction mixture is stirred for several hours at the specific temperature required. Working-up in processes (a) and (b) according to the invention is carried out in each case by customary methods (cf. the preparation examples).

The active compounds according to the invention can be used as defoliants, desiccants, agents for destroying broad-leaved plants and, especially, as weed-killers. By weeds, in the broadest sense, thee are to be understood all plants which grow in locations where they are undesired. Whether the substances according to the invention act as total or selective herbicides depends essentially on the mount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cypems, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Aspera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations; coffee plantations, tea plantations, robber plantations, oil palm plantations, cocoa plantations, soft fruit plantings and hopfields, in lawns, turf and pasture-land, and for the selective combating of weeds in annual cultures.

The compounds of the formula (I) according to the invention are particularly suitable for selectively combating dicotyledon weeds in monocotyledon cultures, especially by the post-emergence method.

The active compounds can be converted into the customary formulation, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carders, optionally with the use of surface-active agents, that is emulsifying agents and/or dispersing agents and/or foam-forming agents.

In the case of the me of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carders for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulation in general comprise between 0.1 and 95 per cent by weight of active compound, preferably between 0.5 and 90%.

For combating weeds, the active compounds according to the invention, as such or in their formulations, can also be used as mixtures with known herbicides, finished formulation or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluoroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor, dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkyoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, diallate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

PREPARATION EXAMPLES

Example 1

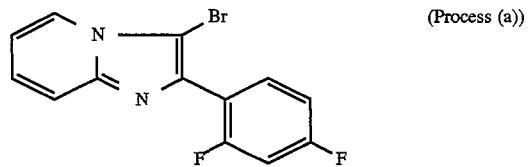

(Process (a))

1.6 g (10 mmol) of bromine are added to a solution of 2.6 g (10 mmol) of 2-(2,4-difluorophenyl)-imidazo-[1,2-a]-pyridine hydrochloride in 100 ml of chloroform, and the mixture is stirred for 18 hours at 20° C. It is then washed using 5% strength aqueous sodium hydrogen sulphite solution and subsequently water, dried using sodium sulphate and filtered. The solvent is carefully removed from the filtrate by distillation under a water pump vacuum.

2.0 g (65% of theory) of 3-bromo-2-(2,4-difluorophenyl)-imidazo-[1,2-a]-pyridine are obtained as a crystalline product of melting point 144° C.

Example 2

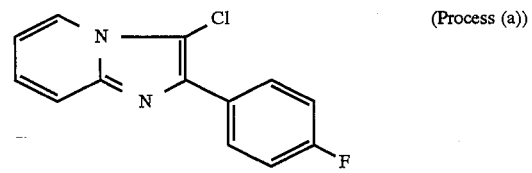

(Process (a))

A mixture of 2.3 g (10 mmol) of 2-(4-fluorophenyl)-imidazo-[1,2-a]-pyridine hydrochloride, 1.6 g (12 mmol) of N-chloro-succinimide and 100 ml of chloroform is refluxed at the boil for 10 hours. After cooling, the solution is washed using 5% strength aqueous sodium carbonate solution and then filtered over silica gel. The filtrate is concentrated under a water pump vacuum, the residue is stirred with diisopropyl ether and the solid product obtained is isolated by filtration with suction.

0.4 g (16% of theory) of 3-chloro-2-(4-fluorophenyl)-imidazo-[1,2-a]-pyridine is obtained.

$^1$H NMR (DMSO-D$_6$, δ): 8.56 ppm.

Example 3

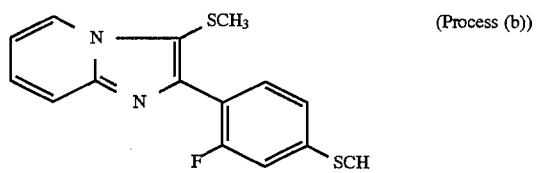

(Process (b))

A mixture of 2.5 g (8.1 mmol) of 3-bromo-2-(2,4-difluorophenyl)-imidazo-[1,2-a]pyridine, 1.9 g (27 mmol) of sodium methylmercaptide and 50 ml of dimethylformamide is refluxed at the boil for 18 hours. The reaction mixture is then diluted with water to the approximately three-fold volume and shaken with ethyl acetate. The solvent is then carefully removed from the organic phase by distillation under a water pump vacuum.

1.0 g (40% of theory) of 3-methylthio-2-(2-fluoro-4-methylthio-phenyl)-imidazo-[1,2-a]pyrimidine is obtained as an oily residue.

$^1$H NMR (CDCl$_3$, d): 8.43 ppm.

Other examples of the compounds of the formula (I) which can be prepared analogously to Preparation Examples 1 to 3 and following the general description of the preparation processes according to the invention are those listed in Table 1 below.

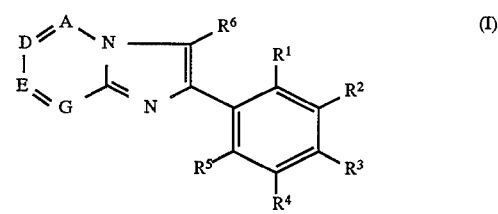

(I)

TABLE 1

Examples of the compounds of the formula (I)

| Ex. No. | A | D | E | G | R$^1$ | R$^2$ | R$^3$ | R$^4$ | R$^5$ | R$^6$ | Melting point (°C.) |
|---|---|---|---|---|---|---|---|---|---|---|---|
| 4 | CH | C—CF$_3$ | CH | CH | H | H | F | H | H | Br | 138 |
| 5 | CH | C—CH$_3$ | CH | CH | Cl | H | Cl | H | H | Br | 108 |
| 6 | CH | CH | CH | CH | H | H | F | H | H | Br | 82 |
| 7 | CH | CH | CH | CH | F | H | F | F | H | Br | 172 |
| 8 | CH | CH | CH | CH | H | H | Cl | H | H | Br | 136 |
| 9 | CH | CH | CH | CH | CH$_3$ | H | Cl | CH$_3$ | H | Br | 123 |
| 10 | CH | CH | CH | CH | H | Cl | Cl | H | H | Br | 156 |
| 11 | CH | CH | CH | CH | H | CH$_3$ | Cl | H | H | Br | 78 |
| 12 | CH | C—CF$_3$ | CH | CH | H | H | CN | H | H | Br | 206 |
| 13 | CH | C—CH$_3$ | CH | CH | H | H | Cl | H | H | Br | 104 |
| 14 | CH | C—CF$_3$ | CH | CH | H | H | Cl | H | H | Br | 138 |
| 15 | CH | C—Cl | CH | CH | H | H | Br | H | H | Br | 179 |
| 16 | CH | C—CF$_3$ | CH | CH | H | H | Cl | H | Cl | Br | 118 |
| 17 | CH | C—CF$_3$ | CH | CH | H | H | CH$_3$ | H | H | Br | 235 |
| 18 | CH | C—CF$_3$ | CH | CH | H | H | OCH$_3$ | H | H | Br | (amorphous) |
| 19 | N | C—Cl | CH | CH | F | H | F | F | H | Br | 185 |
| 20 | CH | CH | CH | CH | H | H | H | Cl | H | Br | 115 |
| 21 | CH | CH | CH | CH | Cl | H | H | H | H | Br | 103 |
| 22 | CH | CH | CH | CH | H | H | CN | H | H | Br | 226 |
| 23 | CH | CH | CH | CH | F | H | F | NO$_2$ | H | Br | 199 |
| 24 | CH | CH | CH | CH | F | H | NO$_2$ | F | H | Br | |
| 25 | CH | CH | CH | CH | H | OC$_2$H$_5$ | CN | H | F | Br | |
| 26 | CH | CH | CH | CH | H | —OCH$_2$C≡CH | Cl | H | F | Cl | |
| 27 | CH | CH | CH | CH | H | N(CH$_3$)$_2$ | CN | H | F | Br | |
| 28 | CH | CH | N | N | H | H | F | H | F | Br | 190 |
| 29 | CH | CH | N | N | H | NO$_2$ | F | H | F | Cl | |
| 30 | CH | CH | N | N | H | OC$_2$H$_5$ | CN | H | F | Br | |
| 31 | CH | CH | CH | CH | F | H | H | F | H | Br | 258 |
| 32 | CH | C—CF$_3$ | CH | CH | H | H | CN | H | H | SCH$_3$ | 105 |
| 33 | CH | CH | CH | CH | H | NO$_2$ | Cl | H | H | Br | 192 |
| 34 | CH | CH | CH | CH | H | NO$_2$ | Cl | H | Cl | Br | $^1$H NMR: δ = 8.52 ppm |
| 35 | CH | C—CF$_3$ | CH | CH | H | NO$_2$ | Cl | H | F | Br | |
| 36 | CH | C—Cl | CH | CH | H | NO$_2$ | Cl | H | F | Cl | |
| 37 | CH | CH | CH | CH | H | NO$_2$ | CF$_3$ | H | F | Br | |
| 38 | CH | CH | CH | CH | H | NH$_2$ | F | H | F | Br | 137 |
| 39 | CH | C—CF$_3$ | CH | CH | H | NH$_2$ | F | H | F | Br | |
| 40 | CH | CH | CH | CH | H | NH$_2$ | Cl | H | H | Br | $^1$H NMR: δ = 8.14 ppm |
| 41 | CH | CH | CH | CH | Br | NH$_2$ | Cl | H | Br | Br | $^1$H NMR: |

TABLE 1-continued

Examples of the compounds of the formula (I)

| Ex. No. | A | D | E | G | R¹ | R² | R³ | R⁴ | R⁵ | R⁶ | Melting point (°C.) |
|---|---|---|---|---|---|---|---|---|---|---|---|
| 42 | CH | CH | CH | CH | H | $NH_2$ | Cl | H | Cl | Br | $\delta = 7.58$ ppm ¹H NMR: $\delta = 6.94$ ppm |
| 43 | CH | CH | CH | CH | H | $NH_2$ | Cl | H | F | Br | |
| 44 | CH | CH | CH | CH | H | $NHSO_2CH_3$ | F | H | F | Br | 202 |
| 45 | CH | CH | CH | CH | H | $NHSO_2C_2H_5$ | F | H | F | Br | |
| 46 | CH | CH | CH | CH | H | $NHSO_2CH_3$ | Cl | H | H | Br | |
| 47 | CH | CH | CH | CH | H | $NHSO_2CH_3$ | Cl | H | Cl | Br | 242 |
| 48 | CH | CH | CH | CH | H | $NHSO_2CH_3$ | Cl | H | F | Cl | |
| 49 | CH | CH | CH | CH | H | $NHSO_2C_3H_7$ | $CF_3$ | H | F | Br | |
| 50 | CH | C—$CF_3$ | CH | CH | H | $NHSO_2CH_3$ | F | H | F | Br | |
| 51 | CH | CH | CH | CH | H | $NHSO_2$—C₆H₄—$CH_3$ | F | H | F | Br | |
| 52 | CH | CH | CH | CH | F | H | $CF_3$ | H | H | Br | 82 |
| 53 | CH | CH | CH | CH | F | H | $OC_2H_5$ | H | H | Br | 53 |
| 54 | CH | CH | CH | CH | H | Cl | $COOC_2H_5$ | H | F | Br | 200 |
| 55 | CH | C—$CF_3$ | CH | CH | F | H | F | H | H | Br | 112 |
| 56 | CH | CH | CH | CH | H | $OC_2H_5$ | F | H | F | Br | |
| 57 | CH | CH | CH | CH | H | $SO_3H$ | F | H | F | Br | |
| 58 | CH | CH | CH | CH | H | $SO_2NH_2$ | F | H | F | Br | 174 |
| 59 | CH | CH | CH | CH | H | $SO_2NH_2$ | F | H | F | Cl | 236 |
| 60 | CH | CH | CH | CH | H | $SO_2NH_2$ | Cl | H | H | Br | |
| 61 | CH | C—$CF_3$ | CH | CH | H | $SO_2NH_2$ | Cl | H | H | Br | |
| 62 | CH | CH | CH | CH | H | $SO_2NH_2$ | Cl | H | Cl | Br | |
| 63 | CH | CH | CH | CH | H | $SO_2NH_2$ | $CF_3$ | H | F | Br | |
| 64 | CH | CH | CH | CH | H | $SO_2NH_2$ | Cl | H | F | Cl | |
| 65 | CH | CH | CH | CH | H | $SO_2NHCH_3$ | F | H | F | Cl | |
| 66 | CH | CH | CH | CH | H | $SO_2NHC_3H_7$-i | F | H | F | Br | 181 |
| 67 | CH | CH | CH | CH | H | $SO_2NHC_2H_5$ | Cl | H | H | Cl | |
| 68 | CH | CH | CH | CH | H | $SO_2NHC_3H_7$-i | Cl | H | H | Br | |
| 69 | CH | CH | CH | CH | H | $SO_2NHC_3H_7$-i | Cl | H | Cl | Br | 208 |
| 70 | CH | CH | CH | CH | H | $SO_2NHC_3H_7$-n | Cl | H | F | Br | |
| 71 | CH | CH | CH | CH | H | $SO_2NH$—C₆H₄—Cl | F | H | F | Br | |
| 72 | CH | CH | C—Cl | CH | H | $SO_2N(CH_3)_2$ | F | H | F | Br | |
| 73 | CH | C—$CF_3$ | CH | CH | H | $SO_2N(CH_3)_2$ | | | | | |
| 74 | CH | CH | CH | CH | H | $SO_2N(CH_3)_2$ | F | H | F | Cl | |
| 75 | CH | CH | CH | CH | H | $SO_2N(C_2H_5)_2$ | F | H | F | Br | ¹H NMR: $\delta = 8.33$ ppm |
| 76 | CH | CH | CH | CH | H | $SO_2N(C_3H_7)_2$ | Cl | H | H | Br | |
| 77 | CH | CH | CH | CH | H | $SO_2N(C_2H_5)_2$ | Cl | H | Cl | Br | |
| 78 | CH | CH | CH | CH | H | $SO_2N(C_2H_5)_2$ | $OCH_3$ | H | F | Br | |
| 79 | CH | CH | CH | CH | F | H | F | H | H | $NO_2$ | 172 |
| 80 | CH | CH | CH | CH | H | $NO_2$ | F | H | F | $NO_2$ | 228 |
| 81 | CH | CH | CH | CH | Cl | H | Cl | H | H | Br | 135 |
| 82 | CH | CH | CH | CH | H | $SO_2Cl$ | Cl | H | H | Cl | |
| 83 | CH | CH | CH | CH | H | $SO_2OH$ | Cl | H | F | Br | |
| 84 | CH | CH | CH | CH | H | $NO_2$ | Br | H | H | Br | 205 |
| 85 | CH | CH | CH | CH | H | $NH_2$ | Br | H | H | Br | ¹H NMR: $\delta = 8.39$ ppm |
| 86 | CH | CH | CH | CH | H | $NHSO_2CH_3$ | Br | H | H | Br | |
| 87 | CH | CH | CH | CH | H | $COOC_2H_5$ | Cl | H | F | Br | |

The compound listed in Table 1 as Example 38 can be prepared for example as follows.

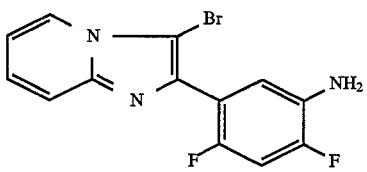

2 g (6.5 mmol) of 3-bromo-2-(2,4-difluorophenyl)-imidazo-[1,2-a]-pyridine are introduced at 0° C. in 6 ml of concentrated sulphuric acid, and 4 g (40.5 mmol) of concentrated nitric acid are added. After stirring of the reaction mixture has been continued for 10 minutes, it is poured into ice-water, and the pH is brought to 2 using 20% strength sodium hydroxide solution. The solid is filtered off with suction and washed thoroughly using water.

2.2 g (95% of theory) of a yellow solid are obtained, and this is employed in the next reaction step without further purification.

5.3 g (17 mmol) of 3-bromo-2-(2,4-difluoro-5-nitrophenyl)-imidazo-[1,2-a]-pyridine in 50 ml of concentrated hydrochloric acid are stirred for 18 hours at room temperature with 15 g (79 mmol) of tin(II) chloride. The reaction mixture is poured into water, and the PH is brought to 9–10 using sodium hydroxide solution. The mixture is subjected to filtration with suction over kieselguhr and subsequently washed with ethyl acetate, and the aqueous phase is extracted. The combined organic phases are chromatographed over silica gel using ethyl acetate. This gives 1.2 g (22% of theory) of 3-bromo-2-(5-amino-2,4-difluorophenyl)-imidazo-[1,2-a]-pyridine of melting point 137° C.

The compound listed in Table 1 as Example 44 can be prepared for example as follows:

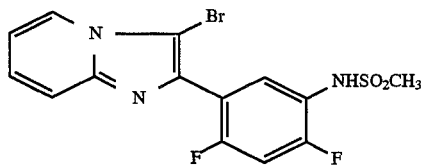

0.5 g (1.5 mmol) of 3-bromo-2-(5-amino-2,4-difluorophenyl)-imidazo-[1,2-a]-pyridine in 5 ml of pyridine and 30 ml of dichloromethane are treated with 0.2 g (1.7 mmol) of methanesulphonyl chloride and the mixture is stirred for 24 hours at room temperature. The mixture is acidified using hydrochloric acid and extracted using chloroform, the aqueous phase is rendered weakly alkaline and reextracted. The alkaline extract is concentrated in vacuo and stirred with diisopropyl ether.

0.5 g (79% of theory) of 3-bromo-2-(5-methylsulphonylamino-2,4-difluorophenyl)-imidazo-[1, 2-a]- pyridine of melting point 202° C. is obtained.

The compounds listed in Table 1 as Example 66 can be prepared for example as follows:

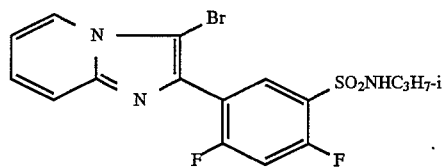

5 ml of chlorosulphonic acid are added to 1.5 g (5 mmol) of 3-bromo-2-(2,4-di-fluorophenyl)-imidazo-[1,2-a]-pyridine and the mixture is heated for 2 hours at 80° C. The mixture is subsequently hydrolysed in ice-water and extracted using dichloromethane, and the organic phase is dried over magnesium sulphate. After the desiccant has been filtered off, 2 ml (23 mmol) of isopropylamine are added, and the mixture is stirred for 18 hours at room temperature. It is washed using 1N hydrochloric acid, dried using magnesium sulphate and filtered. The solvent is carefully removed from the filtrate by distillation.

0.5 g (23% of theory) of 3-bromo-2-(2,4-difluoro-5-isopropyl-amino-sulphonyl-phenyl)-imidazo-[1,2-a]-pyridine of melting point 181° C. is obtained.

Starting Substances of the Formula (II)

Example (II-1)

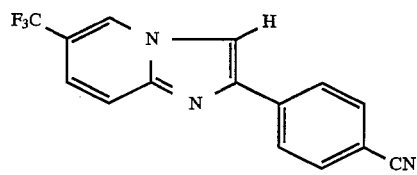

A mixture of 7.5 g (50 mmol) of 2-amino-5-trifluoromethyl-pyridine, 11.2 g (50 mmol) of 4-cyanophenacyl bromide and 200 ml of acetonitrile is refluxed for 36 hours. After cooling, the crystalline product is isolated by filtration with suction.

11.2 g (78% of theory) of 2-(4-cyanophenyl)-5-trifluoromethyl-imidazo-[1,2-a]-pyridine hydrobromic of melting point >300° C. are obtained.

The corresponding free compound can be obtained by stirring the product with aqueous hydrogen carbonate solution and filtration with suction.

Other examples of compounds of the formula (II) which can be obtained analogously to Example (II-1) are those listed in Table 2 below.

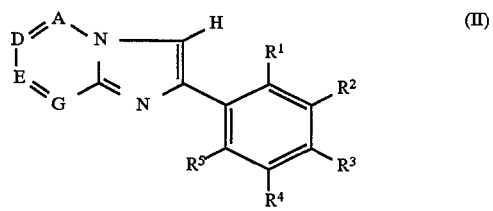

TABLE 2

Examples of the compounds of the formula (II)

| Ex. No. | A | D | E | G | R¹ | R² | R³ | R⁴ | R⁵ | Melting point (°C.) |
|---|---|---|---|---|---|---|---|---|---|---|
| II-2 | CH | CH | CH | CH | F | H | H | F | H | >210*) |
| II-3 | CH | CH | CH | CH | CH₃ | H | Cl | CH₃ | H | 104 |
| II-4 | CH | CH | CH | CH | H | H | Cl | H | H | 186*) |
| II-5 | CH | CH | CH | CH | H | Cl | Cl | H | H | 166 |
| II-6 | CH | CH | CH | CH | H | CH₃ | Cl | H | H | 115 |
| II-7 | CH | CH | CH | CH | H | H | H | Cl | H | 240*) |

*)obtained as the hydrogen bromide addition product

USE EXAMPLES

Example A

Post Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compounds in such a way as to apply the particular amounts of active compound desired per unit area. The concentration of the spray liquor is chosen so that the particular amounts of active compound desired are applied in 2,000 l of water/ha. After three weeks, the degree of damage to the plants is rated in % damage in comparison to the development of the untreated control.

The figures denote:

0%=no action (like untreated control)

100%=total destruction

In this test, a powerful action against weeds such as Abutilon (70–95%), Datura (95–100%), Portulaca (70–100%) and Solanum (80–100%) is shown, for example, by the compounds of Preparation Examples 1, 6, 7 and 8 at an application rate of 500 g/ha, combined with a very good tolerance by crop plants such as wheat (in each case 0%).

We claim:

1. An imidazoazine of the formula (I)

in which $R^1$ represents hydrogen, halogen, cyano, carboxyl, carbamoyl, nitro, alkyl, halogenoalkyl, alkoxy or halogenoalkoxy, $R^2$ represents hydrogen, halogen, cyano, carboxyl, nitro, hydroxyl, mercapto, amino, carbamoyl, sulpho, sulphamoyl, chlorosulphonyl, or represents in each case optionally substituted alkyl, alkenyl, alkinyl, alkoxy, alkenyloxy, alkinyloxy, alkylthio, alkenylthio, alkinylthio, alkylsulphinyl, alkylsulphonyl, alkylaminosulphonyl, dialkylaminosulphonyl, alkylamino, dialkylamino, alkenylamino, alkinylamino, alkylsulphonylamino, N-alkylalkylsulphonylamino, alkoxycarbonyl, alkoxyaminosulphonyl, N-alkyl-alkoxy-aminosulphonyl, arylsulphonylamino, arylalkylsulphonylamino, N-alkyl-arylsulphonylamino, N-alkyl-arylalkylsulphonylamino, arylaminosulphonyl, arylalkylaminosulphonyl, N-alkyl-arylaminosulphonyl or N-alkyl-arylalkylaminosulphonyl, $R^3$ represents hydrogen, halogen, cyano, carboxyl, amino, hydroxyl, carbamoyl, nitro, or represents in each case optionally substituted alkyl, alkenyl, alkinyl, alkoxy, alkenyloxy, alkinyloxy, alkylthio, alkenylthio, alkinylthio, alkylsulphinyl, alkylsulphonyl, alkylamino, alkenylamino, alkinylamino, alkylsulphonylamino or alkoxycarbonyl, $R^4$ represents hydrogen, halogen, cyano, alkyl or halogenoalkyl, $R^5$ represents hydrogen, halogen, cyano, alkyl or halogenoalkyl, $R^6$ represents halogen, cyano, nitro, amino, alkoxy, alkylthio, alkylsulphinyl, alkylsulphonyl, alkylamino or dialkylamino, A represents nitrogen or the group C—$R^7$, D represents nitrogen or the group C—$R^8$, E represents nitrogen or the group C—$R^9$ and G represents nitrogen or the group C—$R^{10}$, where $R^7$, $R^8$, $R^9$ and $R^{10}$ are identical or different and in each case represent hydrogen, halogen, cyano, carboxyl, carbamoyl, nitro, or in each case optionally substituted alkyl, phenyl, alkoxy, alkylthio, alkylsulphinyl, alkylsulphonyl, alkylamino, dialkylamino or alkoxycarbonyl, or an acid addition product thereof, with the proviso that at least one of the radicals $R^1$ to $R^5$ is other than hydrogen and that the following compounds are excepted by disclaimer:

3-Bromo-2-(4-methylsulphonyl-phenyl)-imidazo-[1,2-a]-pyridine, 3-bromo-2-(4-formyl-phenyl)-imidazo-[1,2-a]-pyridine, 3-bromo-2-(4-nitro-phenyl)-imidazo-[1,2-a]-pyridine, 3-chloro-2-(4-bromo-phenyl)-imidazo-[1,2-a]-pyridine, 3-chloro-2-(4-chloro-phenyl)-imidazo-[1,2-a]-pyridine, 3-chloro-2-(4-methoxy-phenyl)-imidazo-[1,2-a]-pyridine, 3-bromo-2-(4-bromo-phenyl)-imidazo-[1,2-a]-pyridine and 3-bromo-2-(4-methoxy-phenyl)-imidazo-[1,2-a]-pyridine.

2. An imidazoazine according to claim 1, characterized in that $R^1$ represents hydrogen, fluorine, chlorine, bromine, cyano, carboxyl, carbamoyl, nitro, or represents alkyl or alkoxy, each of which has 1 to 4 carbon atoms and each of which is optionally substituted by fluorine or chlorine, $R^2$ represents hydrogen, fluorine, chlorine, bromine, cyano, carboxyl, carbamoyl, nitro, hydroxyl, mercapto, amino, sulpho, sulphamoyl, chlorosulphonyl, or represents alkyl, alkoxy, alkylthio or alkylamino, each of which has 1 to 6 carbon atoms and each of which is optionally substituted by fluorine, chlorine, cyano, carboxyl, carbamoyl or $C_1$–$C_4$-alkoxy-carbonyl, $R^2$ furthermore represents alkenyl, alkinyl, alkenyloxy, alkinyloxy, alkenylthio, alkinylthio, alkenylamino or alkinylamino, each of which has 3 to 6 carbon atoms and each of which is optionally substituted by fluorine, chlorine, bromine, cyano, carboxyl, carbamoyl or $C_1$-$C_4$-alkoxy-carbonyl, $R^2$ furthermore represents alkylsulphinyl, alkylsulphonyl, alkylsulphonylamino, N-alkyl-alkylsulphonylamino, alkylaminosulphonyl, dialkylaminosulphonyl, alkoxyaminosulphonyl, N-alkyl-alkoxyaminosulphonyl, dialkylamino or alkoxycarbonyl, each of which has up to 6 carbon atoms in the alkyl groups and each of which is optionally substituted by fluorine or chlorine, $R^2$ furthermore represents in each case optionally substituted phenylsulphonylamino, phenyl-$C_1$-$C_4$-alkylsulphonylamino, N—$C_1$-$C_4$-alkcyl-phenylsulphonylamino, N—$C_1$-$C_4$-alkyl-phenyl-$C_1$-$C_4$-alkyl-sulphonylamino, phenylaminosulphonyl, phenyl-$C_1$-$C_4$-alkyl-aminosulphonyl, N—$C_1$-$C_4$-alkyl-phenylaminosulphonyl or N—$C_1$-$C_4$-alkyl-phenyl-$C_1$-$C_4$-alkyl-aminosulphonyl, it being possible for the phenyl groups in each case optionally to contain the following substituents: fluorine, chlorine, bromine, iodine, cyano, nitro, hydroxyl, amino, carboxyl, carbamoyl, and in each case optionally fluorine and/or chlorine-substituted $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, $C_1$-$C_4$-alkoxycarbonyl or phenyl, $R^3$ represents hydrogen, fluorine, chlorine, bromine, cyano, carboxyl, amino, hydroxyl, carbamoyl, nitro, or represents alkyl, alkoxy, alkylthio or alkylamino, each of which has 1 to 6 carbon atoms and each of which is optionally substituted by fluorine, chlorine, cyano, carboxyl, carbamoyl or $C_1$-$C_4$-alkoxy-carbonyl, $R^3$ furthermore represents alkenyl, alkinyl, alkenyloxy, alkinyloxy, alkenylthio, alkinylthio, alkenylamino or alkinylamino, each of which has 3 to 6 carbon atoms and each of which is optionally substituted by fluorine, chlorine, bromine, cyano, carboxyl, carbamoyl or $C_1$-$C_4$-alkoxy-carbonyl, or represents alkylsulphinyl, alkylsulphonyl, alkylsulphonylamino or alkoxycarbonyl, each of which has up to 6 carbon atoms and each of which is optionally substituted by fluorine or chlorine, $R^4$ represents hydrogen, fluorine, chlorine, bromine, cyano, or represents alkyl having 1 to 6 carbon atoms which is optionally substituted by fluorine or chlorine, $R^5$ represents hydrogen, fluorine, chlorine, bromine, cyano, or represents alkyl having 1 to 4 carbon atoms which is optionally substituted by fluorine or chlorine, $R^6$ represents chlorine, bromine, iodine, cyano, nitro, amino, or represents alkoxy, alkylthio, alkylsulphinyl, alkylsulphonyl, alkylamino or dialkylamino, each of which has 1 to 6 carbon atoms in the alkyl groups, A represents nitrogen or the group C—$R^7$, D represents nitrogen or the group C—$R^8$, E represents nitrogen or the group C—$R^9$ and G represents nitrogen or the group C—$R^{10}$, where $R^7$, $R^8$, $R^9$ and $R^{10}$ are identical or different and each of which represents hydrogen, fluorine, chlorine, bromine, cyano, carboxyl, carbamoyl, nitro, or in each case optionally fluorine- or chlorine-substituted alkyl, phenyl, alkoxy, alkylthio, alkylsulphinyl, alkylsulphonyl, alkylamino, dialkylamino or alkoxycarbonyl, the alkyl radicals in each case containing 1 to 6 carbon atoms, with the proviso that at least one of the radicals $R^1$ to $R^5$ is other than hydrogen and with the exception of the compounds excluded in claim 1 by disclaimer, and or an acid addition product thereof wherein said addition product is formed with a protonic acid.

3. An imidazoazine according to claim 1, characterized in that $R^1$ represents hydrogen, fluorine, chlorine, bromine, cyano, nitro, methyl, ethyl or trifluoromethyl, $R^2$ represents hydrogen, fluorine, chlorine, bromine, cyano, carboxyl, carbamoyl, nitro, hydroxyl, mercapto, amino, sulpho, sulphamoyl, chlorosulphonyl, or represents methyl, ethyl, propyl, methoxy, ethoxy, propoxy, methylthio, ethylthio, propylthio, methylamino, ethylamino or propylamino, each of which is optionally substituted by fluorine, chlorine, cyano, carboxyl, carbamoyl, methoxycarbonyl or ethoxycarbonyl, $R^2$ furthermore represents allyl, propargyl, allyloxy, propargyloxy, allylthio, propargylthio, dimethylamino, allylamino or propargylamino, each of which is optionally substituted by fluorine, chlorine, cyano, carboxyl, methoxycarbonyl or ethoxycarbonyl, or represents methylsulphinyl, ethylsulphinyl, methylsulphonyl, ethylsulphonyl, methylsulphonylamino, ethylsulphonylamino, n- or i-propylsulphonylamino, methylaminosulphonyl, ethylaminosulphonyl, n- or i-propylaminosulphonyl, dimethylaminosulphonyl, diethylaminosulphonyl, dipropylaminosulphonyl, phenylsulphonylamino, tolylsulphonylamino, phenylaminosulphonyl, tolylaminosulphonyl, methoxycarbonyl or ethoxycarbonyl, each of which is optionally substituted by fluorine or chlorine, $R^3$ represents hydrogen, fluorine, chlorine, bromine, cyano, carboxyl, amino, hydroxyl, carbamoyl, nitro, or represents methyl, ethyl, n- or i-propyl, n-, i-, s- or t-butyl, methoxy, ethoxy, propoxy, methylthio, ethylthio, propylthio, methylamino, ethylamino or propylamino, each of which is optionally substituted by fluorine, chlorine, cyano, carboxyl, carbamoyl, methoxycarbonyl or ethoxycarbonyl, $R^3$ furthermore represents allyl, propargyl, allyloxy, propargyloxy, allylthio, propargylthio, allylamino or propargylamino, each of which is optionally substituted by fluorine, chlorine, cyano, carboxyl, methoxycarbonyl or ethoxycarbonyl, or represents methylsulphinyl, ethylsulphinyl, methylsulphonyl, ethylsulphonyl, methylsulphonylamino, ethylsulphonylamino, methoxycarbonyl or ethoxycarbonyl, each of which is optionally substituted by fluorine or chlorine, $R^4$ represents hydrogen, fluorine, chlorine, bromine, cyano, methyl, ethyl or trifluoromethyl, $R^5$ represents hydrogen, fluorine, chlorine, bromine, cyano, methyl, ethyl or trifluoromethyl, $R^6$ represents chlorine, bromine, cyano, nitro, amino, methoxy, ethoxy, methylthio, ethylthio, methylsulphinyl, ethylsulphinyl, methylsulphonyl, ethylsulphonyl, methylamino or dimethylamino, A represents nitrogen or the group C—$R^7$, D represents nitrogen or the group C—R$^8$, E represents nitrogen or the group C—R$^9$, and G represents nitrogen or the group C—R$^{10}$, where R$^7$, R$^8$, R$^9$ and R$^{10}$ are identical or different and in each case represent hydrogen, fluorine, chlorine, bromine, cyano, carboxyl, carbamoyl, nitro, or in each case optionally fluorine- or chlorine-substituted methyl, ethyl, n- or i-propyl, phenyl, methoxy, ethoxy, methylthio, ethylthio, methylsulphinyl, ethylsulphinyl, methylsulphonyl, ethylsulphonyl, methylamino, ethylamino, dimethylamino, diethylamino, methoxycarbonyl or ethoxycarbonyl, with the proviso that at least one of the radicals R$^1$ to R$^5$ is other than hydrogen and with the exception of the compounds excluded in claim 1 by disclaimer, or an acid addition product wherein said product is formed with a hydrohalic acid.

4. An imidazoazine according to claim 1, characterized in that

A represents the group C—R$^7$,

D represents the group C—R$^8$,

E represents the group C—R$^9$ and

G represents the group C—R$^{10}$, where R$^1$, R$^2$, R$^3$, R$^4$, R$^5$, R$^6$, R$^7$, R$^8$, R$^9$ and R$^{10}$ have the meanings mentioned in claim 1, with the proviso that at least one of the radicals R$^1$ to R$^5$ is other than hydrogen and with the exception of the compounds excluded in claim 1 by disclaimer.

5. An imidazoazine according to claim 3, characterized in that

A represents the group C—R$^7$,

D represents the group C—R$^8$,

E represents the group C—R$^9$ and

G represents the group C—R$^{10}$, where R$^1$, R$^2$, R$^3$, R$^4$, R$^5$, R$^6$, R$^7$, R$^8$, R$^9$ and R$^{10}$ have the meanings mentioned in claim 1, with the proviso that at least one of the radicals R$^1$ to R$^5$ is other than hydrogen and with the exception of the compounds of excluded by disclaimer.

6. A process for the preparation of the imidazoazines of the formula

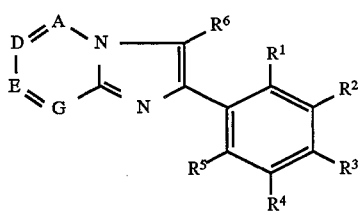

(I)

in which

R$^1$, R$^2$, R$^3$, R$^4$, R$^5$, R$^6$, A, D, E and G have the meanings given in claim 1, where R$^7$, R$^8$, R$^9$ and R$^{10}$ are identical or different and in each case represent hydrogen, halogen, cyano, carboxyl, carbamoyl, nitro, or in each case optionally substituted alkyl, phenyl, alkoxy, alkylthio, alkylsulphinyl, alkylsulphonyl, alkylamino, dialkylamino or alkoxycarbonyl, and acid addition products of the compounds of the formula (I), with the proviso that at least one of the radicals R$^1$ to R$^5$ is other than hydrogen and that the following compounds are excepted by disclaimer: 3-bromo-2-(4-methylsulphonyl-phenyl)-imidazo-[1,2-a]-pyridine, 3-bromo-2-(4-formyl-phenyl)-imidazo-[1,2-a]-pyridine, 3-bromo-2-(4-nitro-phenyl)-imidazo[1,2-a]-pyridine, 3-chloro-2-(4-bromo-phenyl)-imidazo-[1,2-a]-pyridine, 3-chloro-2-(4-chloro-phenyl)-imidazo-[1,2-a]-pyridine, 3-chloro-2-(4-methoxy-phenyl)-imidazo-[1,2-a]-pyridine, 3-bromo-2-(4-bromo-phenyl)-imidazo-[1,2-a]pyridine and 3-bromo-2-(4-methoxy-phenyl)-imidazo-[1,2-a]-pyridine, characterized in that, (a) in the event that, in formula (I), R$^6$ represents halogen or nitro and R$^1$, R$^2$, R$^3$, R$^4$ and R$^5$ as well as A, D, E and G have the abovementioned imidazoazines of the general formula (II)

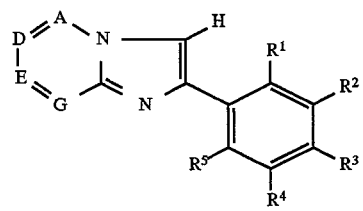

in which

R$^1$, R$^2$, R$^3$, R$^4$, R$^5$, A, D, E and G have the abovementioned meanings, are reacted with halogenating agents or nitrating agents, if appropriate in the presence of inert diluents, or in that, (b) in the event that, in formula (I), R$^6$ represents amino, cyano, alkoxy, alkylthio, alkylsulphinyl, alkylsulphonyl, alkylamino or dialkylamino and R$^1$, R$^2$, R$^3$, R$^4$, R$^5$, A, D, E and G have the abovementioned meanings, halogenated imidazoazines of the general formula (Ia)

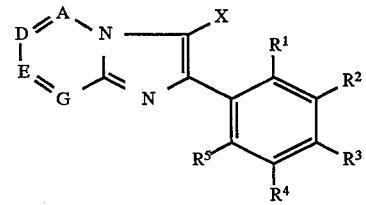

in which

X represents halogen and

R$^1$, R$^2$, R$^3$, R$^4$, R$^5$, A, D, E and G have the abovementioned meanings, are reacted with ammonia or with alkali metal cyanides or with alcohols, alkylmercaptans, alkylamines or dialkylamines or with their alkali metal salts, if appropriate in the presence of diluents, and, if appropriate—to prepare corresponding alkylsulphinyl or alkysulphonyl compounds—, the product is subsequently oxidized by customary methods, and when, if appropriate—to prepare acid addition products of the compounds of the formula (I)—, the compounds obtained in accordance with process (a) or (b) are reacted with acids by customary methods.

7. An imidazoazine according to claim 2 wherein the protonic acid is HCl, HBr, HI, $H_2SO_4$, methanesulphonic acid, benzenesulphonic acid, p-tolunesulphonic acid and napththalene-1,5-disulphonic acid.

8. An imidazoazine according to claim 3, wherein the hydrohalic acid is HCl or HBr.

9. A herbicidal composition which comprises an effective amount of an imidazoazine according to claim 1 and an inert carrier.

10. A method of combatting undesired plants which comprises applying to said plants or to their environment an effective amount of a compound according to claim 1.

11. A compound according to claim 1, wherein the compound is

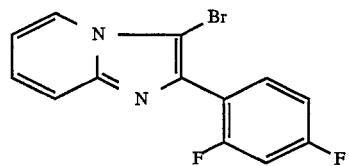

* * * * *

UNITED STATES PATENT AND TRADEMARK OFFICE
CERTIFICATE OF CORRECTION

PATENT NO. : 5,658,857
DATED : August 19, 1997
INVENTOR(S) : Andree, et al.

It is certified that error appears in the above-indentified patent and that said Letters Patent is hereby corrected as shown below:

Col. 22, line 13   After " abovementioned " insert -- meanings, --

Col. 19, line 16   Delete " $N-C_1-C_4$-allcyl- " and substitute -- $N-C_1-C_4$-alkyl --

Signed and Sealed this

Seventeenth Day of March, 1998

Attest:

BRUCE LEHMAN

*Attesting Officer*   *Commissioner of Patents and Trademarks*